United States Patent
Baig et al.

(10) Patent No.: US 11,135,142 B2
(45) Date of Patent: *Oct. 5, 2021

(54) DENTIFRICE COMPOSITIONS COMPRISING TIN IONS

(71) Applicant: The Procter & Gamble Company, Cincinnati, OH (US)

(72) Inventors: Arif Ali Baig, Mason, OH (US); Tammy K. Baker, South Lebanon, OH (US); Samuel James St. John, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/911,414

(22) Filed: Jun. 25, 2020

(65) Prior Publication Data

US 2020/0405594 A1 Dec. 31, 2020

Related U.S. Application Data

(60) Provisional application No. 62/867,907, filed on Jun. 28, 2019.

(51) Int. Cl.

| *A61K 8/19* | (2006.01) |
|---|---|
| *A61K 8/21* | (2006.01) |
| *A61K 8/25* | (2006.01) |
| *A61K 8/27* | (2006.01) |
| *A61K 8/34* | (2006.01) |
| *A61Q 11/00* | (2006.01) |
| *A61K 8/81* | (2006.01) |

(52) U.S. Cl.
CPC ............. *A61K 8/19* (2013.01); *A61K 8/21* (2013.01); *A61K 8/25* (2013.01); *A61K 8/27* (2013.01); *A61K 8/345* (2013.01); *A61K 8/8111* (2013.01); *A61Q 11/00* (2013.01); *A61K 2800/48* (2013.01); *A61K 2800/59* (2013.01); *A61K 2800/91* (2013.01)

(58) Field of Classification Search
CPC . A61K 8/21; A61K 8/25; A61K 8/345; A61K 8/27; A61K 8/8111; A61K 2800/48; A61K 2800/91; A61K 2800/59; A61K 8/19; A61K 8/20; A61Q 11/00

See application file for complete search history.

(56) References Cited

U.S. PATENT DOCUMENTS

| 5,348,733 | A | 9/1994 | Morishima |
| 9,011,825 | B2 * | 4/2015 | Midha ............ A61K 8/21 424/52 |
| 9,687,427 | B2 | 6/2017 | Li et al. |
| 10,195,124 | B2 | 2/2019 | Prencipe |
| 10,213,368 | B2 | 2/2019 | Li et al. |
| 2003/0007937 | A1 | 1/2003 | Lawlor |
| 2008/0286214 | A1 | 11/2008 | Brown |
| 2008/0311055 | A1 | 12/2008 | Futterer |
| 2012/0276023 | A1 | 11/2012 | Shimohirao |
| 2014/0037555 | A1 | 2/2014 | Hoke |
| 2014/0227202 | A1 | 8/2014 | Pilgaonkar |
| 2016/0324738 | A1 * | 11/2016 | Baig ............ A61K 8/27 |
| 2017/0105911 | A1 | 4/2017 | Budde |
| 2017/0157171 | A1 | 6/2017 | Gerard |
| 2017/0333310 | A1 | 11/2017 | Subramanyam |
| 2018/0214356 | A1 | 8/2018 | Hilke |
| 2020/0405593 | A1 | 12/2020 | Baig et al. |
| 2020/0405595 | A1 | 12/2020 | Gupta et al. |

FOREIGN PATENT DOCUMENTS

| EP | 0514966 A2 | 11/1992 |
| EP | 2057978 A1 | 5/2009 |
| GB | 2216005 A | 10/1989 |
| WO | 9509602 A1 | 4/1995 |
| WO | 9712523 A1 | 4/1997 |
| WO | 0132135 A1 | 5/2001 |
| WO | 2015105438 A1 | 7/2015 |
| WO | 2016178652 A1 | 11/2016 |

OTHER PUBLICATIONS

PCT Search Report and Written Opinion for PCT/US2020/070178 dated Sep. 17, 2020.
PCT Search Report and Written Opinion for PCT/US2020/070179 dated Oct. 6, 2020.
PCT Search Report and Written Opinion for PCT/US2020/070186 dated Oct. 20, 2020.
PCT Search Report—PCT/CN2019/093507 dated Jun. 28, 2019.
All Office Actions, U.S. Appl. No. 16/911,412.
All Office Actions, U.S. Appl. No. 16/911,415.

* cited by examiner

*Primary Examiner* — Snigdha Maewall
(74) *Attorney, Agent, or Firm* — Parker D. McCrary

(57) ABSTRACT

A dentifrice composition with tin, calcium, and a pH of greater than 7. A dentifrice composition with tin, fluoride, calcium abrasive, water, and a pH of greater than 7. Dentifrice compositions with a high tin ion availability. Dentifrice compositions comprising stannous fluoride and/or stannous chloride in combination with calcium carbonate.

14 Claims, No Drawings

DENTIFRICE COMPOSITIONS COMPRISING TIN IONS

FIELD OF THE INVENTION

The present invention relates to compositions comprising tin and calcium. The present invention also relates to compositions comprising stannous fluoride and calcium carbonate.

BACKGROUND OF THE INVENTION

Sources of tin ions, such as stannous fluoride, are added to dentifrice compositions to deliver antimicrobial and anti-sensitivity benefits. However, tin ion sources can be difficult to incorporate into dentifrice compositions due to (i) the reactivity between tin ions and other dentifrice components, such as silica, and (ii) the formation of insoluble tin compounds at particular pH conditions. Thus, the incorporation of tin Ions into dentifrice compositions is only possible by minimizing interactions between tin ions and key dentifrice components during storage to maximize tin ion availability for reactivity with oral cavity surfaces, such as enamel, dentine, gums, plaque, and bacteria.

The chemical instability in solution of tin ions can be mitigated by lowering the pH of the solution, providing anionic chelants, such as anions of organic acids, or providing polymeric chelants, such as polyphosphates or polycarboxylates. Some of these chelants can also prevent tin ion interactions with the surface of silica molecules by instead binding directly to the tin ions. However, strong chelant-tin ion interactions can also be detrimental to tin ion availability if the chelant-tin ion interactions are stronger than binding affinity between tin ions and intra oral surfaces, such tin ion delivery is a prerequisite for performance against diseases of the oral cavity such as plaque, gingivitis, malodor, caries, sensitivity, and dental erosion etc. Thus, even chelant selection must be balanced with the overall dentifrice formulation to maximize tin ion availability.

Additionally, the selected abrasive system can influence the tin ion availability. For example, calcium abrasives, such as calcium pyrophosphate and dicalcium phosphate, can interact with tin ions generated from stannous fluoride to result in a loss of up to 90% of the available tin ions over the life of a dentifrice. Switching from a calcium phosphate-based abrasive to a silica abrasive system can improve the amount of available tin ions, but will still result in only up to 50% available tin ions due to surface interactions between the tin ion and the silica abrasive. A 50% tin ion availability is still significant enough to require supplemental sources of tin ions to be added, such as stannous chloride, to compensate for the reactivity between the tin ions and the surface of the silica abrasive. Other approaches include hydrophobic modification of the silica surface, heat treating the silica to remove reactive surface hydroxyl functional groups or formulating the dentifrice with minimal or no water to prevent reactivity between the abrasive and free tin ions. However, each of these strategies to mitigate the loss of free tin ions in solution, and be available to interact with the oral cavity, results in higher costs, limiting commercial viability of these approaches. Therefore, there is a need for a dentifrice composition that provides a source of available tin ions at an affordable cost.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Disclosed herein is a dentifrice composition comprising from about 0.0025% to about 5%, by weight of the dentifrice composition, of a tin ion source, from about 10% to about 50%, by weight of the dentifrice composition, of a calcium abrasive, and less than about 5%, by weight of the dentifrice composition, of water, wherein the dentifrice composition has a pH of greater than 7.

Disclosed herein is a dentifrice composition comprising from about 0.0025% to about 5%, by weight of the dentifrice composition, of a tin ion source, from about 0.0025% to about 5%, by weight of the dentifrice composition, of a fluoride ion source, the fluoride ion source comprising sodium fluoride, sodium monofluorophosphate, amine fluoride, or combinations thereof, from about 10% to about 50%, by weight of the dentifrice composition, of calcium carbonate, and from about 10% to about 45%, by weight of the dentifrice composition, of water, wherein the dentifrice composition has a pH of greater than 7.

Disclosed herein is a dentifrice composition comprising from about 0.01% to about 5%, by weight of the dentifrice composition, of a tin ion source, from about 10% to about 50%, by weight of the dentifrice composition, of calcium carbonate, and from about 5% to about 75%, by weight of the dentifrice composition, of water, wherein the dentifrice composition has a pH of greater than 7 and wherein the dentifrice composition has about 70% or greater of available tin ions after three months at 40° C.

DETAILED DESCRIPTION OF THE INVENTION

The present invention is directed to dentifrice compositions comprising a tin ion source and a calcium abrasive. Additionally, the present invention is directed to dentifrice compositions comprising stannous fluoride and calcium carbonate.

While the formation of $CaF_2$ is desired in the oral cavity, many dentifrice formulations do not employ calcium ions and fluoride ions in aqueous dentifrice compositions because $CaF_2$ can precipitate out of solution during storage, thereby eliminating any benefit derived from calcium or fluoride ions. For example, calcium carbonate ($CaCO_3$) is an abrasive of choice to minimize dentifrice formulation costs. However, due to the incompatibility between free fluoride and calcium ions, almost all $CaCO_3$ based formulations use sodium monofluorophosphate salt as a less reactive fluoride source.

In addition to the possibility of premature $CaF_2$ formations, using $CaCO_3$ in combination with a tin ion source can also raise the pH of the dentifrice composition, which can lead to the precipitation of $Sn(OH)_2$ out of the dentifrice composition, thereby eliminating any benefit derived from free tin ions.

As such, dentifrice compositions comprising a tin ion source and a calcium abrasive are typically not expected to be compatible due to the possibility for the formation of $CaF_2$ and $Sn(OH)_2$, which can precipitate out of the dentifrice composition. Unexpectedly, and as described herein, stable dentifrice compositions comprising a tin ion source and a calcium abrasive at a pH of greater than 7 has been found to be shelf stable with minimal or no formation of $CaF_2$ and/or $Sn(OH)_2$. Additionally, the stable dentifrice compositions have been found to have greater than about 80% of available tin ions and/or greater than about 80% of available fluoride ions even after several months. Without wishing to be bound by theory, it is believed that when dentifrice compositions comprising a tin ion source and a calcium abrasive are properly formulated, the amount of available tin ions can be increased relative to dentifrice compositions comprising a tin ion source and a silica abrasive. Additionally, the dentifrice compositions described herein would comprise components with lower costs to increase the commercial viability of such an approach.

While the specification concludes with claims particularly pointing out and distinctly claiming the invention, it is believed that the present invention will be better understood from the following description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

The term "oral care composition", as used herein, includes a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice composition", as used herein, includes tooth or subgingival-paste, gel, or liquid formulations unless otherwise specified. The dentifrice composition may be a single-phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "orally acceptable carrier" comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy. The carriers or excipients of the present invention can include the usual and conventional components of mouthwashes or mouth rinses, as more fully described hereinafter: Mouthwash or mouth rinse carrier materials typically include, but are not limited to one or more of water, alcohol, humectants, surfactants, and acceptance improving agents, such as flavoring, sweetening, coloring and/or cooling agents.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a bleaching agent."

All measurements referred to herein are made at about 23° C. (i.e. room temperature) unless otherwise specified.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, and so forth.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such.

The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The dentifrice composition can be in any suitable form, such as a solid, liquid, powder, paste, or combinations thereof. The oral care composition can be dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The components of the dentifrice composition can be incorporated into a film, a strip, a foam, or a fiber-based dentifrice composition. The dentifrice composition can include a variety of active and inactive ingredients, such as, for example, but not limited to a tin ion source, a calcium abrasive, water, a fluoride source, zinc ion source, one or more polyphosphates, humectants, surfactants, other ingredients, and the like, as well as any combination thereof, as described below.

Tin

The dentifrice composition of the present invention comprise tin. The tin can be provided by a tin ion source. The tin ion source can be any suitable compound that can provide tin ions in a dentifrice composition and/or deliver tin ions to the oral cavity when the dentifrice composition is applied to the oral cavity. The tin ion source can comprise one or more tin containing compounds, such as stannous fluoride, stannous chloride, stannous bromide, stannous iodide, stannous oxide, stannous oxalate, stannous sulfate, stannous sulfide, stannic fluoride, stannic chloride, stannic bromide, stannic iodide, stannic sulfide, and/or mixtures thereof. Preferably, the tin ion source can comprise stannous fluoride, stannous chloride, and/or mixture thereof.

The dentifrice composition can comprise from about 0.0025% to about 5%, from about 0.2% to about 1%, from about 0.5% to about 1.5%, or from about 0.3% to about 0.6%, by weight of the dentifrice composition, of a tin ion source.

Calcium Abrasive

The dentifrice composition of the present invention comprises calcium. The calcium can be provided by a calcium abrasive. Abrasives can be added to dentifrice formulations to help remove surface stains from teeth. The calcium abrasive can be any suitable abrasive compound that can provide calcium ions in a dentifrice composition and/or deliver calcium ions to the oral cavity when the dentifrice composition is applied to the oral cavity.

The dentifrice composition can comprise from about 5% to about 70%, from about 10% to about 50%, from about 10% to about 60%, from about 20% to about 50%, from about 25% to about 40%, or from about 1% to about 50% of a calcium abrasive. The calcium abrasive can comprise one or more calcium abrasive compounds, such as calcium carbonate, precipitated calcium carbonate (PCC), ground calcium carbonate (GCC), chalk, dicalcium phosphate, calcium pyrophosphate, and/or mixtures thereof.

The dentifrice composition can comprise an additional non-calcium abrasive, such as bentonite, silica gel (by itself, and of any structure), precipitated silica, amorphous precipitated silica (by itself, and of any structure as well), hydrated silica, perlite, titanium dioxide, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the dentifrice compositions to tailor the polishing characteristics of the target dentifrice formulation. The dentifrice composition can comprise from about 5% to about 70%, from about 10% to about 50%, from about 10% to about 60%, from about 20% to about 50%, from about 25% to about 40%, or from about 1% to about 50%, by weight of the dentifrice composition, of the non-calcium abrasive Alternatively, the dentifrice composition can be substantially free of, essentially free of, or free of silica, alumina, or any other non-calcium abrasive. The dentifrice composition can comprise less than about 5%, less than about 1%, less than about 0.5%, less than about 0.1%, or 0% of a non-calcium abrasive, such as silica and/or alumina.

Polyol

The oral care compositions of the present invention can comprise polyol. A polyol is an organic compound with more than one hydroxyl functional groups. The polyol can be any suitable compound that can weakly associate, interact, or bond to tin ions while the oral care composition is stored prior to use. The polyol can be a sugar alcohol, a monosaccharide, a disaccharide, a polysaccharide, or a non-reducing sugar. Sugar alcohols are a class of polyols that can be obtained through the hydrogenation of sugar compounds with the formula $(CHOH)_nH_2$, where n=4-6. Preferably, n is 5 and/or 6 because these compounds have been shown to unexpectedly interact with tin ion sources to create soluble complexes, as described herein.

The polyol can be glycerin, erythritol, xylitol, sorbitol, mannitol, butylene glycol, lactitol, galactitol, and/or combinations thereof. Preferably, the polyol can be a sugar alcohol with the formula $(CHOH)_nH_2$, where n=4-6. More preferably, the polyol can be a sugar alcohol with the formula $(CHOH)_nH_2$, where n=5 and/or 6. Even more preferably, the polyol can be xylitol, sorbitol, galactitol, and/or mixtures thereof.

The oral care composition can comprise 0.01% to about 70%, from about 5% to about 70%, from about 5% to about 50%, from about 10% to about 60%, or from about 20% to about 80%, by weight of the oral care composition, of a polyol.

The oral care composition can also comprise an additional humectant, have low levels of an additional humectant, be substantially free of, essentially free, or be free of an additional humectant. Humectants, in general, serve to add body or "mouth texture" to an oral care composition or dentifrice as well as preventing the oral care composition from drying out. Suitable humectants include polyethylene glycol (at a variety of different molecular weights), propylene glycol, glycerin, erythritol, xylitol, sorbitol, mannitol, butylene glycol, lactitol, hydrogenated starch hydrolysates, and/or mixtures thereof. The oral care composition can comprise a polyol and an additional humectant, such as xylitol to interact with the tin ion source and glycerin to prevent the oral care composition from drying out during storage or add body to the oral care composition. The oral care composition can also be free of an additional humectant because the polyol can serve as both the polyol and the additional humectant, such as when the polyol is xylitol, sorbitol, or combinations thereof.

The oral care composition can comprise one or more humectants each at a level of from about 0.01% to about 70%, from about 5% to about 50%, from about 10% to about 60%, or from about 20% to about 80%, by weight of the oral care composition.

Water

The dentifrice composition of the present invention can be anhydrous, a low water formulation, or a high water formulation. In total, the oral care composition can comprise from 0% to about 99%, from about 5% to about 75%, about 20% or greater, about 30% or greater, or about 50% or greater by weight of the composition, of water. Preferably, the water is USP water.

In a high water dentifrice formulation, the dentifrice composition comprises from about 45% to about 75%, by weight of the composition, of water. The high water dentifrice composition can comprise from about 45% to about 65%, from about 45% to about 55%, or from about 46% to about 54%, by weight of the composition, of water. The water may be added to the high water dentifrice formulation and/or may come into the composition from the inclusion of other ingredients.

In a low water dentifrice formulation, the dentifrice composition comprises from about 5% to about 45%, by weight of the composition, of water. The low water dentifrice composition can comprise from about 5% to about 35%, from about 10% to about 25%, or from about 20% to about 25%, by weight of the composition, of water. The water may be added to the low water dentifrice formulation and/or may come into the composition from the inclusion of other ingredients.

In an anhydrous dentifrice formulation, the dentifrice composition comprises less than about 10%, by weight of the composition, of water. The anhydrous dentifrice composition comprises less than about 5%, less than about 1%, or 0%, by weight of the composition, of water. The water may be added to the anhydrous formulation and/or may come into the dentifrice composition from the inclusion of other ingredients.

The dentifrice composition can also comprise other orally acceptable carrier materials, such as alcohol, humectants, polymers, surfactants, and acceptance improving agents, such as flavoring, sweetening, coloring and/or cooling agents.

pH

The dentifrice composition can comprise one or more buffering agents. Buffering agents, as used herein, refer to agents that can be used to adjust the slurry pH of the dentifrice compositions to a range of greater than 7, from greater than 7 to about 14, about 7.5 or greater, about 8 or greater, from about 7.5 to 10, greater than 7 to about 10, or from about 8 to about 10. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. The dentifrice composition can comprise one or more buffering agents each at a level of from about 0.1% to about 30%, from about 1% to about 10%, or from about 1.5% to about 3%, by weight of the present composition.

Zinc

The dentifrice composition can comprise zinc. The zinc can be provided by a zinc ion source. The zinc ion source can comprise one or more zinc containing compounds, such as zinc fluoride, zinc lactate, zinc oxide, zinc phosphate, zinc chloride, zinc acetate, zinc hexafluorozirconate, zinc sulfate, zinc tartrate, zinc gluconate, zinc citrate, zinc malate, zinc glycinate, zinc pyrophosphate, zinc metaphosphate, zinc oxalate, and/or zinc carbonate.

The zinc ion source may be present in the total dentifrice composition at an amount of from about 0.01% to about 5%, from about 0.2% to about 1%, from about 0.5% to about 1.5%, or from about 0.3% to about 0.6%, by weight of the dentifrice composition.

Fluoride

The dentifrice composition can comprise fluoride. The fluoride can be provided by a fluoride ion source. The fluoride ion source can comprise one or more fluoride containing compounds, such as stannous fluoride, sodium fluoride, potassium fluoride, amine fluoride, sodium monofluorophosphate, zinc fluoride, and/or mixtures thereof.

The fluoride ion source and the tin ion source can be the same compound, such as for example, stannous fluoride, which can generate tin ions and fluoride ions. Additionally, the fluoride ion source and the tin ion source can be separate compounds, such as when the tin ion source is stannous chloride and the fluoride ion source is sodium monofluorophosphate or sodium fluoride.

The fluoride ion source and the zinc ion source can be the same compound, such as for example, zinc fluoride, which can generate zinc ions and fluoride ions. Additionally, the fluoride ion source and the zinc ion source can be separate compounds, such as when the zinc ion source is zinc phosphate and the fluoride ion source is stannous fluoride.

The dentifrice composition can comprise a fluoride ion source capable of providing from about 50 ppm to about 5000 ppm, and preferably from about 500 ppm to about 3000 ppm of free fluoride ions. To deliver the desired amount of fluoride ions, the fluoride ion source may be present in the total dentifrice composition at an amount of from about 0.0025% to about 5%, from about 0.2% to about 1%, from about 0.5% to about 1.5%, or from about 0.3% to about 0.6%, by weight of the dentifrice composition.

Polyphosphates

The dentifrice composition can comprise polyphosphate. The polyphosphate can be provided by a polyphosphate source. A polyphosphate source can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. Alkali earth metal cations, such as calcium, are not preferred because they tend to form insoluble fluoride salts from aqueous solutions comprising a fluoride ions and alkali earth metal cations. Thus, the dentifrice compositions disclosed herein can be free of or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Astaris.

The dentifrice composition can comprise from about 0.01% to about 15%, from about 0.1% to about 10%, from about 0.5% to about 5%, from about 1 to about 20%, or about 10% or less, by weight of the dentifrice composition, of the polyphosphate source.

Humectants

The dentifrice composition can comprise a humectant, have low levels of a humectant, or be free of a humectant. Humectants serve to add body or "mouth texture" to an oral care composition or dentifrice as well as preventing the dentifrice from drying out. Suitable humectants include polyethylene glycol (at a variety of different molecular weights), propylene glycol, glycerin (glycerol), erythritol, xylitol, sorbitol, mannitol, butylene glycol, lactitol, hydrogenated starch hydrolysates, and/or mixtures thereof. The dentifrice composition can comprise one or more humectants each at a level of from 0 to about 70%, from about 5% to about 50%, from about 10% to about 60%, or from about 20% to about 80%, by weight of the dentifrice composition.

Surfactants

The dentifrice composition can comprise one or more surfactants. The surfactants can be used to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants, such as sodium lauryl sulfate, sodium lauryl isethionate, sodium lauroyl methyl isethionate, sodium cocoyl glutamate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine, sodium cocoyl glutamate, and the like. Sodium lauryl sulfate is a preferred surfactant. The dentifrice composition can comprise one or more surfactants each at a level from about 0.01% to about 15%, from about 0.3% to about 10%, or from about 0.3% to about 2.5%, by weight of the dentifrice composition.

Thickening Agents

The dentifrice composition can comprise one or more thickening agents. Thickening agents can be useful in the dentifrice compositions to provide a gelatinous structure that stabilizes the toothpaste against phase separation. Suitable thickening agents include polysaccharides, polymers, and/or silica thickeners. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

The thickening agent can comprise polysaccharides. Polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise one or more polymers. The polymer can be a polyethylene glycol (PEG), a polyvinylpyrrolidone (PVP), polyacrylic acid, a polymer derived from at least one acrylic acid monomer, a copolymer of maleic anhydride and methyl vinyl ether, a crosslinked polyacrylic acid polymer, of various weight percentages of the dentifrice composition as well as various ranges of average molecular ranges.

The thickening agent can comprise inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

The dentifrice composition can comprise from 0.01% to about 15%, from 0.1% to about 10%, from about 0.2% to about 5%, or from about 0.5% to about 2% of one or more thickening agents.

Chelant

The dentifrice composition can comprise one or more chelants, having a molecular weight (MW) of less than 1000. The term "chelant", as used herein means a bi- or multidentate ligand having at least two groups capable of binding to the divalent metal ions. Typically, those chelants useful herein will also form water soluble complexes with the stannous ions. Dentifrice compositions comprising silica abrasives typically include one or more chelants to reversibly bind the tin ions to prevent the tin ions from irreversibly binding to the surface of silica particles. Suitable chelants herein include $C_2$-$C_6$ dicarboxylic and tricarboxylic acids, such as succinic acid, malic acid, tartaric acid and citric acid; $C_3$-$C_6$ monocarboxylic acids substituted with hydroxyl, such as gluconic acid; picolinic acid; amino acids such as glycine; phytic acid, salts thereof and mixtures thereof. Preferably, the chelant is sodium gluconate or a salt of citric acid.

The dentifrice composition can comprise one or more chelants each at a level of from about 0.01% to about 5%, from about 0.2% to about 2%, from about 0.5% to about 1.5%, or from about 1% to about 3%, by weight of the dentifrice composition. Alternatively, the dentifrice composition can be substantially free of, essentially free of, or free of a chelant because the dentifrice compositions of the present invention comprises a calcium abrasive instead of a silica abrasive. Additionally, the dentifrice composition can comprise one or more chelants each at a level of less than about 1%, less than about 0.5%, less than about 0.1%, or less than about 0.01%, by weight of the dentifrice composition.

Other Ingredients

The dentifrice composition can comprise a variety of other ingredients, such as flavoring agents, sweeteners, colorants, preservatives, buffering agents, or other ingredients suitable for use in oral care compositions, as described below.

Flavoring agents also can be added to the dentifrice composition. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") or N-(Ethoxycarbonylmethyl)-3-p-menthanecarboxamide (known commercially as "WS-5"), and mixtures thereof. A flavor system is generally used in the compositions at levels of from about 0.001% to about 5%, by weight of the dentifrice composition. These flavoring agents generally comprise mixtures of aldehydes, ketones, esters, phenols, acids, and aliphatic, aromatic and other alcohols.

Sweeteners can be added to the oral care composition to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, sucralose, stevia, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Preservatives also can be added to the oral care compositions to prevent bacterial growth. Suitable preservatives approved for use in oral compositions such as methylparaben, propylparaben, benzoic acid, and sodium benzoate can be added in safe and effective amounts.

Titanium dioxide may also be added to the present composition. Titanium dioxide is a white powder which adds opacity to the compositions. Titanium dioxide generally comprises from about 0.25% to about 5%, by weight of the dentifrice composition.

Other ingredients can be used in the oral care composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

Ion Availability

The dentifrice composition can be described by its tin ion availability and/or its fluoride ion availability. The dentifrice composition can have a tin ion availability at least about 70%, at least about 75%, at least about 80%, or at least about 85% immediately after mixing, after at least 1 month, after at least two months, or after at least 3 months using an accelerated stability measurement at 40° C. The dentifrice composition can have a fluoride ion availability of at least about 70%, at least about 75%, at least about 80%, or at least about 85% immediately after mixing, after at least 1 month, after at least two months, or after at least 3 months using an accelerated stability measurement at 40° C. 1 month of storage at 40° C. is equivalent to at least 8 months of storage at room temperature (~22-23° C.).

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Experimental Methods
Tin Ion Availability

This method is suitable for determination of soluble tin in oral care toothpaste or dentifrice compositions from about 5 to about 5,000 ppm Sn in the aqueous slurry supernatant. The slurry was prepared by mixing 1 part toothpaste with 3 parts water. An aliquot of slurry was acid digested, diluted, and analyzed by inductively coupled plasma optical emission spectrometry (ICP-OES) for each toothpaste measured. Results are reported here as ppm in the neat aqueous phase of the toothpaste and/or dentifrice.

Several standards and reagents were prepared prior to the beginning of the analysis. A 5% hydrochloric acid/5% Nitric acid rinse solution was prepared by transferring 100 mL each of concentrated HCl and concentrated $HNO_3$ using a graduated cylinder to a 2 L volumetric flask containing about 1 L of ultrapure, 18 MΩ (DI) water. The solution was swirled to mix and diluted to the mark of the graduated flask then mixed well by repeated flask inversion.

A 1000 mg/L tin and 1000 mg/L gallium standard solution were purchased (Sigma Aldrich, Merck KGaA, Darmstadt, Germany) for preparation of the standard solutions according to TABLE 1. A pipet was used to transfer accurate quantities of the standards to a 50 mL volumetric flask while a graduated cylinder was used for the concentrated acids. After transfer, the volumetric flask was filled to the line with DI water and mixed well.

TABLE 1

Soluble Sn Standard Solution Compositions

| Solution | Conc $HNO_3$ (mL) | Conc HCL (mL) | 1000 mg/L Sn Std (mL) | 1000 mg/L Ga Std (mL) |
|---|---|---|---|---|
| Cal Blank | 2.5 | 2.5 | 0 | 0.2 |
| Cal 10 mg/L Sn | 2.5 | 2.5 | 0.5 | 0.2 |
| LLOQ 0.5 mg/L Sn | 2.5 | 2.5 | 0.025 | 0.2 |
| QC 5 mg/L Sn | 2.5 | 2.5 | 0.25 | 0.2 |

Slurries were prepared by weighing 2.00 grams of sample into a tared round bottom 38 mL centrifuge tube containing 10 glass beads. The weight was recorded to a minimum of 0.001 g. Immedicably before slurrying, 6.0 mL of DI water was transferred to the tubes. Tubes were capped and placed on a vortexer, mixing the samples for 60 minutes at 1200 rpm. The tubes were removed from the vortexer immediately following completion of the mixing cycle and placed in a centrifuge. They were centrifuged at 21,000 relative centrifugal force (RCF) for 10 minutes. Immediately following completion of centrifugation, the tubes were removed, and the supernatant was gently mixed by inverting slowly three times making sure the solid plug at the bottom of the centrifuge tube was not disturbed before the sample was decanted. The supernatant was then decanted into a 15 mL screw cap sample tube, making sure most of the supernatant was transferred.

The supernatant samples were then digested by accurately weighing (to 0.001 g) a 0.5 mL aliquot of supernatant into a 50 mL Falcon tube. Then 2.5 mL of concentrated HCl and $HNO_3$ were added. The tubes were covered with a polypropylene watch glass and placed in a preheated block digester at 90° C. for 30 minutes. The samples were removed the from the heat, the watch class was rinsed three times with DI water (with about 1 mL each time), and that rinsate was added to the digested supernatant. The gallium standard (0.2 mL) was pipetted into the digested supernatant and then the supernatant samples were diluted to 50 mL with DI water. The tubes were capped and mixed. A digestion method blank was prepared in the same manner using 0.5 mL of DI water instead of supernatant. A method blank was prepared and analyzed for each set of hot block digestions if more samples were prepared than could fit into the hot block at once.

The ICP-OES (Perkin-Elmer 8300, Waltham, Mass., USA) was operated by a trained and qualified operator with demonstrated capability of running the instrument and accurately determining the quantity of tin in oral care compositions. The ICP-OES operation parameters were selected based on the model and configuration according to the manufacturer's instructions. Samples were analyzed according to the following protocol:
1. The ICP-OES was preheated and optimized according to the manufacturer's guidelines. Recommended system checks were performed. The system was conditioned for 30 minutes prior to analysis by running the HCl/HNO$_3$ rinse solution through the sample introduction system.
2. The method for determining tin using a gallium internal standard at the manufacturer recommended wavelengths, integration times, and observation modes was loaded into the operating computer.
3. The 5% HCl/5% HNO$_3$ rinse solution was used to rinse the sample introduction system between the analysis of each blank, standard, or test solution.
4. Three to five readings were recorded for all solutions during analysis.
5. The calibration blank was analyzed.
6. The 10 ppm Sn standard was measured.
7. The 5 ppm Sn standard was measured.
8. The 0.5 ppm LLOQ tin standard was measured.
9. The method blank was measured.
10. The test solutions were measured.
11. The 5 ppm Sn standard was re-measured after every sixth test solution and after the last sample. Enough standard was made to complete the analysis.
12. The 0.5 ppm LLOQ tin standard was measured at the end of the sample analysis.

The analysis was considered successful if the % relative standard deviation of the replicate readings for the 10 ppm and the 5 ppm tin standards was less than about 3%. The 5-ppm check standard was within 96-104% of its value. The LLOQ was within 75-125% of its value. The method blank showed less tin signal intensity than the LLOQ sample. The recovery of the internal standard in each analyzed solution was within 90-130% of its value.

The soluble tin was determined according to the following formula:

$$\text{Soluble Tin in Composition} = \frac{\text{Sn from ICP}\left(\frac{\mu g}{mL}\right) \times \text{Final volume of test solution (mL)}}{\text{Supernatant Weight (g)}}. \quad \text{FORMULA I}$$

Results here are reported as a percentage of the as added Sn.
Fluoride Ion Availability Formulations A-E were stored at 40° C. in an accelerated stability experiment. Samples of each formulation were analyzed at 1, 2, and/or 3 months. Samples stored at 40° C. for 1 month would be expected to approximate an equivalent sample stored for at least 8 months at room temperature (~22-23° C.).

The fluoride ion availability was determined by making a 1:3 slurry of the selected dentifrice composition in water (1 part paste plus 3 parts water). The dentifrice slurries were centrifuged, and the supernatant was isolated. Equal parts of dentifrice supernatant and ionic strength adjuster buffer TISAB IV (RICCA, Cat #8673-32) were mixed in a separate container. The concentration of fluoride ions were measured with a fluoride ion selective electrode (VWR Symphony, Cat #14002-788) by converting millivolt values to concentration of fluoride ions relative to a calibration curve of standard fluoride ion concentration.

TABLE 2 shows the dentifrice compositions tested. Formulas A and B are inventive examples, which have a calcium abrasive, calcium carbonate. Formula A is a low water dentifrice composition and includes stannous chloride as the tin ion source. Formula B is an anhydrous dentifrice composition and includes stannous fluoride as the tin ion source.

Formulations C, D, and E are comparative examples, which have a silica abrasive, hydrated silica. Formulations C, D, and E are low to moderate dentifrice compositions with a combination of stannous fluoride and stannous chloride as an additional tin ion source due to the expected low tin ion availability based on the interactivity between the silica abrasive and tin ions in solution.

TABLE 2

Dentifrice Compositions

| Ingredient | A (wt %) | B (wt %) | C (wt %) | D (wt %) | E (wt %) |
|---|---|---|---|---|---|
| SnF$_2$ | — | 0.45 | 0.45 | 0.45 | 0.45 |
| SnCl$_2$[a] | 0.55 | — | 0.56 | 0.56 | 0.56 |
| Water | 16.30 | — | 24.05 | 22.75 | 18.48 |
| CaCO$_3$ | 32.00 | 30.00 | — | — | — |
| Hydrated Silica | — | — | 17.50 | 17.50 | 17.50 |
| Glycerin | — | 33.70 | — | — | — |
| PEG 600 | — | 6.00 | — | — | — |
| Sorbitol | 10.86 | — | 46.00 | 46.00 | 46.00 |
| Erythritol | 20.00 | 20.00 | — | — | — |
| Pyrophosphate[b] | — | — | — | — | 3.17 |
| Glass H | — | 5.00 | — | — | — |
| Na Gluconate | 1.00 | 0.65 | — | 1.30 | — |
| SLS[c] | 1.30 | 1.20 | — | — | — |
| SLS[d] | — | — | 4.60 | 4.60 | 4.60 |
| Urea | 5.00 | — | — | — | — |
| Botanical blend | 0.50 | — | — | — | — |
| NaOH[e] | 0.33 | — | 1.40 | 1.40 | 3.80 |
| Na$_3$PO$_4$ | — | 0.50 | — | — | — |
| NaHCO$_3$ | 10.00 | — | — | — | — |
| Saccharin | 0.50 | 0.25 | 0.50 | 0.50 | 0.50 |
| Sucralose | — | — | 0.06 | 0.06 | 0.06 |
| TiO$_2$ | — | 0.50 | 0.50 | 0.50 | 0.50 |
| Flavor | 1.00 | 1.00 | 1.00 | 1.00 | 1.00 |
| Silica Z-165[f] | — | — | 1.00 | 1.00 | 1.00 |
| Carrageenan | 0.44 | — | 1.50 | 1.50 | 1.50 |
| Xanthan Gum | 0.22 | — | 0.88 | 0.88 | 0.88 |
| Carbomer[g] | — | 0.75 | — | — | — |

[a]SnCl$_2$ with 10% w/w silica;
[b]Sodium acid pyrophosphate (Na$_2$H$_2$P$_2$O$_7$);
[c]SLS powder;
[d]SLS solution 28% w/w in water;
[e]NaOH solution 50% w/w in water;
[f]Thickening silica ZEODENT® 165;
[g]Carbopol® 956

TABLE 3

Available Tin Ions during Accelerated Stability at 40° C. for Formula A

| Duration | Soluble Sn (% theoretical) | Slurry p |
|---|---|---|
| Initial | 85 | 8.61 |
| 1 month | 83 | 8.65 |
| 3 months | 81 | 8.67 |

TABLE 3 shows the percent available tin ions after an accelerated stability study for Formula A. Initially, Formula A had a slurry pH of 8.61 and 85% of the theoretical tin ion amount, or the amount of tin ions added to the composition. The tin ion availability dropped to 83% and 81% after 1 and 3 months, respectively, after being stored at 40° C. Storage of the compositions at 40° C. for 1 month is expected to project the stability of the composition at room temperature (~22-23° C.) for at least 8 months. Thus, tin ions are stable in compositions comprising a calcium abrasive, such as calcium carbonate, for at least 24 months if stored at room temperature (~22-23° C.).

TABLE 4

Available Tin Ions during Accelerated Stability at 40° C. for Formula B

| Duration | Soluble Sn (% theoretical) | Soluble F (% theoretical) | Slurry pH |
|---|---|---|---|
| Initial | 83.2 | 93 | 7.38 |
| 1 month | 85.0 | 84 | 7.40 |
| 2 months | 86.4 | 84 | 7.44 |
| 3 months | 96.5 | 85 | 7.47 |

TABLE 4 shows the percent available tin ions and available fluoride ions after an accelerated stability study for Formula B. Initially, Formula B had a slurry pH of 7.38 and 83% the theoretical tin ion amount, or the amount of tin ions added to the composition. The tin ion availability was 85%, 86%, and 97% after 1, 2, and 3 months, respectively, which, as described above, would project to be 8, 16, and 24 months at room temperature (~22-23° C.). Thus, tin ions are stable in compositions comprising a calcium abrasive, such as calcium carbonate.

Initially, Formula B had 93% of the theoretical fluoride ion amount, or the amount of fluoride ions added to the composition. The fluoride ion availability was 84%, 84%, and 85% after 1, 2, and 3 months respectively. Thus, fluoride ions are unexpectedly stable in compositions comprising a calcium abrasive, such as calcium carbonate.

TABLE 5

Available Tin Ions during Accelerated Stability at 40° C. for Formula C-E

| | Formula C | | Formula D | | Formula E | |
|---|---|---|---|---|---|---|
| Duration | Available Sn (% theoretical) | Slurry pH | Available Sn (% theoretical) | Slurry pH | Available Sn (% theoretical) | Slurry pH |
| Initial | 30.29 | 8.16 | 39.04 | 8.00 | 64.01 | 9.18 |
| 1 month | 18.38 | 8.26 | 23.64 | 8.10 | 42.59 | 9.14 |
| 2 months | 17.68 | 8.16 | 19.33 | 8.00 | 36.31 | 9.12 |

TABLE 5 shows the percent available tin ions after an accelerated stability study for Formula C, D, and E. Initially, Formula C had a slurry pH of 8.18 and 30% of the theoretical tin ion amount, or the amount of tin ions added to the composition. The tin ion availability was 18% and 18% after 1 month and 2 months, respectively. Initially, Formula D had a slurry pH of 8.00 and 39% the theoretical tin ion amount, or the amount of tin ions added to the composition. The tin ion availability was 24% and 19% after 1 month and 2 months, respectively. Initially, Formula E had a slurry pH of 9.18 and 64% the theoretical tin ion amount, or the amount of tin ions added to the composition. The tin ion availability was 43% and 36% after 1 month and 2 months, respectively. As shown in TABLE 5, there was a significant loss of tin ions even at room temperature (initial values). The loss of tin ions continued after 1 month at 40 C. The relatively higher values for Formula D and E are due to better binding of tin ions by the chelants gluconate and pyrophosphate, which help minimize reactivity with silica and stabilize the tin ions against oxidation and hydrolysis by bonding with tin ions.

Importantly, the tin ion availability was much higher in compositions comprising a calcium carbonate abrasive, i.e. Formula A and Formula B, than in compositions comprising a silica abrasive, i.e. Formula C-E. TABLE 3 and TABLE 4 show tin ion availabilities of at least about 80% of the theoretical tin ion amount. In contrast, Formula C-E only had tin ion availabilities of from 18% to 36% of the theoretical tin amount after two months of accelerated stability at 40° C. Thus, replacing a silica abrasive with a calcium carbonate abrasive can improve the tin ion availability by as much as 450% (from 18% to 86%). Thus, the findings in TABLE 2-5 demonstrated that stannous ions are chemically stable at a pH of greater than 7 when combined with a calcium abrasive. Additionally, stannous ions are non-reactive to calcium abrasives, such as calcium carbonate, unlike with silica abrasives. Specifically, the results in TABLE 3 & 4 indicated that stannous ions are unexpectedly stability in compositions comprising calcium carbonate.

While it was expected that interactions between the calcium ions from a calcium abrasive would react with and diminish the amount of available fluoride ions from a fluoride ion source, Formula B, which comprises calcium carbonate and stannous fluoride, had a fluoride ion availability of 93% initially and 85% after 3 months of accelerated stability at 40° C.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A dentifrice composition comprising:
    (a) tin;
    (b) from about 10% to about 60%, by weight of the dentifrice composition, of calcium abrasive; and
    (c) from about 5% to about 45%, by weight of the dentifrice composition, of water, wherein the dentifrice composition has a pH of greater than 7 and wherein the dentifrice composition is shelf stable at about 22-23° C. with no formation of $CaF_2$ and $Sn(OH)_2$.

2. The dentifrice composition of claim 1, wherein the calcium abrasive comprises calcium carbonate.

3. The dentifrice composition of claim 1, wherein the dentifrice composition has about 70% or greater of available tin ions after three months at 40° C.

4. The dentifrice composition of claim 1, wherein the dentifrice composition comprises zinc.

5. The dentifrice composition of claim 1, wherein the dentifrice composition comprises silica abrasive.

6. The dentifrice composition of claim 1, wherein the dentifrice composition comprises humectant.

7. The dentifrice composition of claim 6, wherein the humectant comprises glycerin, sorbitol, erythritol, xylitol, butylene glycol, propylene glycol, polyethylene glycol, or combinations thereof.

8. The dentifrice composition of claim 1, wherein the dentifrice composition comprises from about 0.01% to about 15%, by weight of the dentifrice composition, of one or more surfactants.

9. The dentifrice composition of claim 1, wherein the dentifrice composition comprises about 1% or less, by weight of the dentifrice composition, of silica.

10. The dentifrice composition of claim 1, wherein the dentifrice composition comprises thickening agent.

11. The dentifrice composition of claim 10, wherein the thickening agent comprises xanthan gum, carrageenan, a polyethylene glycol, a crosslinked polyacrylic acid polymer, polyvinyl pyrrolidone, fatty alcohols, or combinations thereof.

12. The dentifrice composition of claim 1, wherein the tin comprises stannous fluoride, stannous chloride, or combinations thereof.

13. The dentifrice composition of claim 1, wherein the dentifrice composition comprises fluoride.

14. The dentifrice composition of claim 13, wherein the fluoride comprises sodium fluoride, stannous fluoride, sodium monofluorophosphate, amine fluoride, zinc fluoride, or combinations thereof.

\* \* \* \* \*